United States Patent
Kokaji

(10) Patent No.: US 9,970,849 B2
(45) Date of Patent: *May 15, 2018

(54) METHOD FOR SEPARATING TARGET ENTITIES FROM A SAMPLE USING A COMPOSITION OF MONO-SPECIFIC TETRAMERIC ANTIBODY COMPLEXES COUPLED TO A SURFACE

(71) Applicant: Stemcell Technologies Inc., Vancouver (CA)

(72) Inventor: Andy Isamu Kokaji, Vancouver (CA)

(73) Assignee: StemCell Technologies Inc., Vancouver, British Columbia (CA)

( * ) Notice: Subject to any disclaimer, the term of this patent is extended or adjusted under 35 U.S.C. 154(b) by 95 days.

This patent is subject to a terminal disclaimer.

(21) Appl. No.: 14/601,367

(22) Filed: Jan. 21, 2015

(65) Prior Publication Data

US 2015/0204765 A1 Jul. 23, 2015

Related U.S. Application Data

(60) Provisional application No. 61/929,581, filed on Jan. 21, 2014.

(51) Int. Cl.
*G01N 33/543* (2006.01)
*G01N 1/40* (2006.01)
*G01N 33/68* (2006.01)

(52) U.S. Cl.
CPC .......... *G01N 1/405* (2013.01); *G01N 33/543* (2013.01); *G01N 33/54326* (2013.01); *G01N 33/6854* (2013.01)

(58) Field of Classification Search
CPC .......... G01N 33/543; G01N 33/54326; G01N 33/6854
See application file for complete search history.

(56) References Cited

U.S. PATENT DOCUMENTS

| | | | |
|---|---|---|---|
| 4,868,109 A * | 9/1989 | Lansdorp | C07K 16/468 424/136.1 |
| 6,008,002 A | 12/1999 | Bodey | |
| 7,135,335 B2 * | 11/2006 | Thomas | C07K 16/28 422/534 |
| 7,160,723 B2 | 1/2007 | Collins et al. | |
| 2006/0024824 A1 * | 2/2006 | Woodside | B03C 1/01 435/366 |
| 2013/0316373 A1 | 11/2013 | Bosio et al. | |
| 2014/0302483 A1 * | 10/2014 | Kauling | B01D 21/00 435/2 |
| 2016/0068811 A1 * | 3/2016 | Kokaji | C12N 5/0636 435/372.3 |
| 2016/0187241 A1 * | 6/2016 | Kokaji | A23L 2/52 435/7.24 |

FOREIGN PATENT DOCUMENTS

WO WO00/73794 A2 12/2000
WO WO2013/076070 A1 5/2013

OTHER PUBLICATIONS

Grutzkau, A. and Radbruch, A., "Small But Mighty: How the MACS (R)—Technology Based on Nanosized Superparamagnetic Particles has Helped to Analyze the Immune System Within the Last 20 Years", Cytometry Part A, vol. 77, No. 7, p. 643-647, May 20, 2010 (online publication).
Peters, C.E. et al., "Isolation of Subsets of Immune Cells", Methods in Molecular Biology, 2005, vol. 302, p. 95-115.
Imada et al., "Promotive effect of macrophage colony-stimulating factor on long-term engraftment of murine hematopoietic stem cells", Cytokine, Academic Press Ltd. Philadelphia, PA, US, vol. 31, No. 6, p. 447-453, 2005.
Hiraoka, A. et al., "Stem Cell Growth Factor; In Situ Hybridization Analysis on the Gene Expression, Molecular Characterization and In Vitro Proliferative Activity of a Recombinant Preparation on Primitive Hematopoietic Progenitor Cells", Hematology Journal, McMillan, Basingstoke, GB, vol. 2, No. 5, p. 307-315, 2001.

* cited by examiner

*Primary Examiner* — Gailene Gabel
(74) *Attorney, Agent, or Firm* — Bereskin & Parr LLP/S.E.N.C.R.L. s.r.l.; Micheline Gravelle

(57) ABSTRACT

An improved method for the preparation of target specific surfaces and uses thereof is described. In particular, the surfaces are bound to mono-specific tetrameric antibody complexes prior to their addition to a sample containing target entities and separating them from non-target entities.

14 Claims, 3 Drawing Sheets

METHOD FOR SEPARATING TARGET ENTITIES FROM A SAMPLE USING A COMPOSITION OF MONO-SPECIFIC TETRAMERIC ANTIBODY COMPLEXES COUPLED TO A SURFACE

This application claims the benefit under 35 USC § 119(e) from U.S. provisional patent application Ser. No. 61/929,581, filed on Jan. 21, 2014, which is incorporated herein by reference.

FIELD

The present disclosure relates to methods for separating cells using mono-specific tetrameric antibody complexes coupled to a surface.

BACKGROUND

In many applications it is desirable to enrich, or alternatively deplete, certain cell populations in a biological sample. The fields of hematology, immunology and oncology rely on samples of peripheral blood and cell suspensions from related tissues such as bone marrow, spleen, thymus and fetal liver. The separation of specific cell types from these heterogeneous samples is key to research in these fields. Purified populations of immune cells such as T cells and B cells are necessary for the study of immune function and are used in immunotherapy. Investigation of the cellular, molecular and biochemical processes require analysis of certain cell types in isolation. Numerous techniques have been used to isolate or deplete erythrocytes, lymphocyte subsets such as T cells, B cells and natural killer (NK) cells and granulocytes such as neutrophils, basophils and eosinophils.

Hematopoietic cells and immune cells have been separated on the basis of physical characteristics such as density and through direct targeting with monoclonal antibodies and a solid surface such as magnetic particles. There are two basic approaches to separating cell populations from peripheral blood and related cell suspensions using monoclonal antibodies. They differ in whether it is the desired or undesired cells which are distinguished/labelled with the antibody(s). In positive selection techniques, the desired cells are labelled with antibodies and removed from the remaining unlabelled/undesired cells. In negative selection, the undesired cells are labelled and removed. Antibody and complement treatment and the use of immunotoxins is a negative selection technique, whereas fluorescence assisted cell sorting (FACS) and most bulk immunoadsorption techniques can be adapted to both positive and negative selection. In immunoadsorption techniques, cells are selected with monoclonal antibodies and preferentially bound to a surface which can be removed from the remainder of the cells e.g. column of beads, flasks, non-magnetic and magnetic particles. Immunoadsorption techniques have won favour clinically and in research because they maintain the high specificity of targeting cells with monoclonal antibodies, but unlike FACS, they can be scaled up to deal directly with the large numbers of cells in a clinical harvest and they avoid the dangers of using cytotoxic reagents such as immunotoxins and complement.

Magnetic separation is a process used to selectively retain magnetic materials within a vessel, such as a centrifuge tube or column, in a magnetic field gradient. Targets of interest, such as specific biological cells, proteins and nucleic acids, can be magnetically labeled by binding of magnetic particles to the surface of the targets through specific interactions including immuno-affinity interactions. Other useful interactions include drug-drug receptor, antibody-antigen, hormone-hormone receptor, growth factor-growth factor receptor, carbohydrate-lectin, nucleic acid sequence-complementary nucleic acid sequence, enzyme-cofactor or enzyme-inhibitor binding. The suspension, containing the targets of interest within a suitable vessel, is then exposed to magnetic field gradients of sufficient strength to separate the targets from other entities in the suspension. The vessel can then be washed with a suitable fluid to remove the unlabeled entities, resulting in a purified suspension of the targets of interest.

The advent of monoclonal antibodies against cell surface antigens has greatly expanded the potential to distinguish and separate distinct cell types. The majority of magnetic labeling systems use supramagnetic particles with monoclonal antibodies or streptavidin covalently bound to their surface. In cell separation applications these particles can be used for either positive selection, where the desired cells are magnetically labeled, or negative selection where the majority of undesired cells are magnetically labeled. Magnetic separation applications where the targets of interest are proteins or nucleic acids would be considered positive selection approaches since the target entity of interest is typically captured on the magnetic particle.

Several commercial cell separation products are available that utilize a magnetic particle directly coupled to antibodies (Miltenyi Biotec Inc., Gladbach, Germany, Life Technologies Corp., Carlsbad, USA, BD Biosciences, San Jose, USA.). Other approaches utilize the labelling of target cells with specific antibodies conjugated to biotin followed by the addition of streptavidin coated magnetic particles that bind the biotinylated antibodies (Miltenyi Biotec, Inc. Life Technologies, BD Biosciences, and STEMCELL Technologies Inc., Vancouver, Canada). Another example is the EasySep™ cell separation system (STEMCELL Technologies Inc.) whereby a bi-specific tetrameric antibody complex is used to crosslink magnetic particles to cells of interest. Tetrameric antibody complexes (TAC) are comprised of two monoclonal antibodies from a first species held in tetrameric array by two antibodies from a second species that bind to the Fc-fragment of the antibodies from the first species (See U.S. Pat. No. 4,868,109 to Lansdorp, which is incorporated herein by reference for a description of TACs and methods for preparing the same).

In the preparation of bi-specific TACs, three different TACs can be formed which comprise the final antibody composition. If an equivalent concentration of two different antibodies (A and B) from the first animal species are combined with an equimolar amount of the crosslinking antibody from the second animal species (C), 25% will be mono-specific TAC for antibody A, 25% will be mono-specific TAC for the second antibody B, and 50% of the TAC will be bi-specific for antibodies A and B. The ratio of each antibody from the first species can be manipulated to skew the ratio of mono-specific to bi-specific TACs to the first or second antibody specific for their respective target antigens.

As used in the current invention, a mono-specific TAC is specific for a single target entity. In one embodiment, the mono-specific TAC contains two identical antibodies from the first animal species that recognize the same antigenic epitope held in a tetrameric array by two antibodies from a second animal species that recognize the Fc-fragment of the first animal species. In another embodiment, the mono-specific TAC contains two different antibody clones from the first animal species that recognize different epitopes on the same target antigen that are held in a tetrameric array by two antibodies from a second animal species that recognize the Fc-fragment of the first animal species. In yet another embodiment, the mono-specific TAC contains two different antibody clones from the first animal species that recognize different antigens expressed on the same target entity that are held in a tetrameric array by two antibodies from a second animal species that recognize the Fc-fragment of the first animal species.

The mono-specific TAC can increase the valency of the complex for its target entity as the TAC would have four antigen binding sites compared to just two with a single IgG antibody molecule.

Patents describing antibodies directly coupled to particles either directly or indirectly via an intermediate receptor-ligand interaction whereby either one of the receptor or ligand are first coupled to the magnetic particle have been described in U.S. Pat. No. 3,970,518A, U.S. Pat. No. 4,230,685, U.S. Pat. No. 8,298,782B2, U.S. Pat. No. 7,160,723B2, and U.S. Pat. No. 5,543,289A which are incorporated herein by reference. In each of these examples, either single or multiple antibodies that recognize a target entity are coupled to particles using conventional techniques that are readily apparent to those skilled in the art such as physical adsorption or chemical conjugation.

Physical adsorption of ligands such as antibodies onto solid surfaces plays a critical role in numerous natural processes and holds great utility in biomaterial applications. Despite efforts and progress in understanding protein adsorption phenomenon at solid surfaces there is widely differing and contradictive explanations as to the observed phenomena that occurs when a protein adsorbs onto a solid surface such as a flask, column of beads, or particles [1]. Protein adsorption onto solid surfaces can be affected by a numerous factors including the pH and ionic strength of the reaction buffer, the temperature of the reaction and the isoelectric point of the protein. In addition, the size, surface charge, reactive moieties on the surface also contribute greatly to the adsorption of the proteins. Once the protein is initially adsorbed or concentrated on the surface, it can be covalently conjugated to said surface.

Depending on the adsorption conditions or conjugation chemistry, the orientation of the antibody can be bound in a conformation that does not allow it to functionally bind to its target antigen. The orientation of the antibodies can be manipulated by modifying the adsorption or conjugation reaction conditions or by the use of an intermediate that is first conjugated to a surface that can help to orient the antibody with the reactive Fab binding domains oriented outwards from the surface (see U.S. Pat. No. 8,298,782 B2 or U.S. Pat. No. 4,230,685). Even in the case of the coupling of an antibody binding intermediate such as protein A or streptavidin, the coupling of said intermediate can also be inefficient resulting in less than ideal coupling efficiency.

In view of the foregoing, there is a need in the art to provide simple and novel methods for improving antibody coupling methods for the preparation of surfaces specific for a target entity for use in fractionating mixtures of target entities and non-target entities.

SUMMARY

The present inventor has developed a method for the coupling of mono-specific tetrameric antibody complexes onto surfaces for use in fractionating mixtures of target entities and non-target entities. The inventor has shown that coupling of mono-specific tetrameric antibody complexes to surfaces is an improvement over existing methods of coupling monoclonal antibodies onto surfaces at equivalent antibody concentrations for fractionating mixtures of target entities and non-target entities.

The advent of monoclonal antibodies against cell surface antigens has greatly expanded the potential to distinguish and separate distinct cell types. Tetrameric antibody complexes (TAC) are comprised of two antibodies from a first animal species held in tetrameric array by two antibodies from a second animal species specific for the Fc-fragment of the first animal species (See U.S. Pat. No. 4,868,109 to Lansdorp, which is incorporated herein by reference for a description of TACs and methods for preparing the same). The method of the disclosure demonstrates the use of mono-specific TAO coupled to a surface such as a magnetic particle for use in fractionating a sample composed of target entities and non-target entities.

A mono-specific TAC is specific for a single type of target entity such as a cell. In one embodiment, the mono-specific TAC contains two identical antibodies from a first animal species that recognize the same antigenic epitope and are held in a tetrameric array by two antibodies from a second animal species that recognize the Fc-fragment of the first animal species. In another embodiment, the mono-specific TAC contains two different antibody clones from a first animal species that recognize different epitopes of the same target antigen and are held in a tetrameric array by two antibodies from a second animal species that recognize the Fc-fragment of the first animal species. In yet another embodiment, the mono-specific TAC contains two different antibody clones from a first animal species that recognize different antigens expressed on the same target entity, such as a cell, that are held in a tetrameric array by two antibodies from a second animal species that recognize the Fc-fragment of the first animal species.

The method of the invention is an unexpected improvement over existing methods as mono-specific TAC coupled surfaces are more effective than monoclonal antibodies coupled to surfaces for the fractionation of target entities from a sample containing target entities and non-target entities.

At equivalent concentrations of target entity specific antibodies, mono-specific TACs coupled surfaces are more effective at fractionating a target entity from a mixture of target and non-target entities.

In one embodiment, the methods of the disclosure can efficiently label and deplete erythrocytes from a complex sample such as human whole blood.

Accordingly, in one embodiment, the present disclosure provides a method for separating target entities from non-target entities in a sample comprising target entities and non-target entities, the method comprising:
 (a) providing at least one mono-specific tetrameric antibody complex (TAC) coupled to a surface, wherein the TAC is specific for the target entities;
 (b) contacting the sample with the TAC coupled surface under conditions to allow binding of the TAO coupled surface to the target entities; and
 (c) separating the target entities TAC coupled surface from the sample to separate the target entities from the non-target entities.

In a one embodiment, the surface is a particle, such as a magnetic particle. A benefit of the magnetic particle approach is that since it is an immunomagnetic cell separation approach, it can be fully automated thereby further reducing sample handling and minimizing exposure to blood borne pathogens such as viruses or parasites.

The target entities can be cells, bacteria, viruses, cell organelles, proteins or nucleic acids.

In one embodiment, the target cells are selected from the group consisting of erythrocytes, lymphocytes, monocytes, granulocytes, tumor cells, stem cells, hematopoietic progenitor cells, mesenchymal cells, mammary epithelial cells, neural cells, endothelial stem cells and embryonic stem cells.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION

Composition and Methods of the Disclosure

Figure 1:
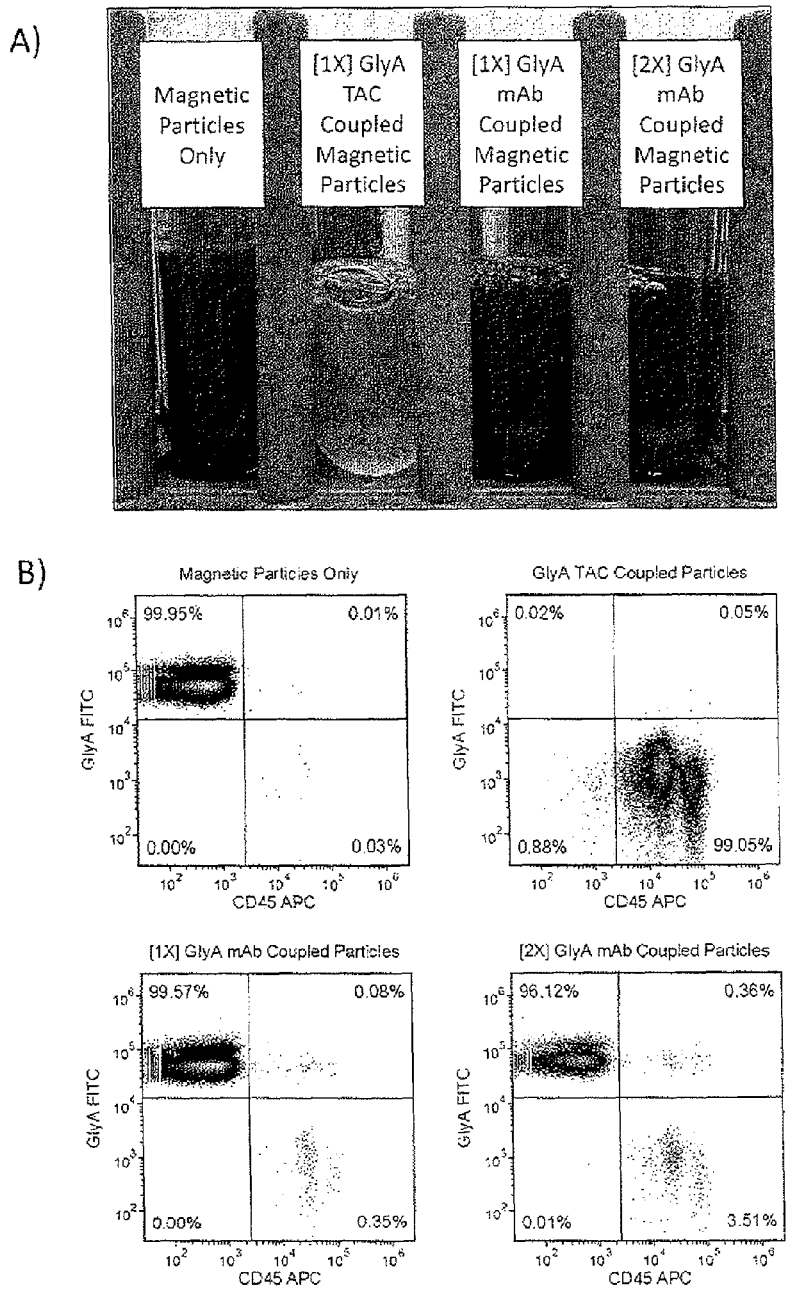
FIG. 1A) shows the depletion of erythrocytes from human peripheral whole blood using carboxydextran magnetic particles coupled to either mono-specific anti-glycophorin A TAC or anti-glycophorin A antibodies. 1B) shows that following erythrocyte depletion using glycophorin-A mono-specific TACs coupled to magnetic particles, 99.05% of enriched cells are CD45+GlyA− compared to 99.95% CD45-GlyA+ when magnetic particles alone are added to human whole blood.

The present disclosure relates to a composition of mono-specific TACs coupled to a surface for use in a method for separating target entities from a sample containing target entities and non-target entities.

In one aspect, the present disclosure provides a method for separating target entities from non-target entities in a sample comprising target entities and non-target entities, the method comprising:
(a) providing at least one mono-specific tetrameric antibody complex (TAC) coupled to a surface, wherein the TAC is specific for the target entities;
(b) contacting the sample with the TAO coupled surface under conditions to allow binding of the TAC coupled surface to the target entities; and
(c) separating the target entities—TAC coupled surface from the sample to separate the target entities from the non-target entities.

The method can be used in both positive and negative selection protocols. In a positive selection protocol, desired entities are removed from a sample. In a negative selection protocol, desired entities remain in the sample following the selection protocol such that the remaining sample is enriched for the desired entities.

As used herein, the term "target entity" is an entity that is to be removed from the sample by the methods described herein. In a preferred embodiment, the target entity is a cell. In a positive selection protocol, the desired cell is the target cell. In a negative selection protocol, the desired cell is not the target cell. Rather, the desired cell is a non-target cell.

In one embodiment, the surface is a particle. The particle can be magnetic or non-magnetic. One example of non-magnetic particles useful in the methods described herein are buoyant particles. Buoyant particles will float when placed in an appropriate buffer, thereby allowing separation of the target cell—TAC coupled particle complexes from a sample.

In a negative selection cell separation protocol, the desired cells are not labeled with the coupled particles and remain in the sample following the removal of the coupled particle labeled target cells. Accordingly, the undesired cells are the "target cells" to be removed from the sample and the desired cells are "non-target cells". In a negative selection cell separation protocol, the mono-specific TAC will contain antibodies specific for the target cells that one wishes to remove from the sample. Accordingly, the present disclosure provides a negative selection cell separation method for enriching and recovering desired cells in a sample containing desired cells and undesired cells comprising:
(a) providing at least one mono-specific TAC coupled to a surface such as a particle, wherein the TAC is specific for the undesired cells;
(b) contacting the sample with the TAC coupled particle under conditions to allow binding of the TAC coupled particles to the undesired cells; and
(c) separating the target cell—TAC coupled particle complexes from the sample to obtain a sample enriched for the desired cells.

In a positive selection protocol, the desired cells are the target cells. In a positive selection, the antibody composition will contain at least one antibody specific for the desired cells that one wishes to remove from the sample. Accordingly, the present disclosure provides a positive selection method for recovering desired cells from a sample containing the desired cells and undesired cells comprising:
(a) providing at least one mono-specific TAC coupled to a surface, wherein the TAC binds to the desired cell particle;
(b) contacting the sample with the TAC coupled particle under conditions to allow binding of the TAC coupled particles to the desired cells;
(c) separating the desired cell—TAC coupled particle complexes from the sample to obtain a second sample enriched for the desired cells bound to the coupled particles; and
(d) washing the desired cell—TAC coupled particle complexes to obtain a sample purified for the desired cells bound to the coupled particles.

In one embodiment, the positive selection method includes the disaggregation of the desired cell—TAC coupled particle complex to separate the desired cells from the coupled particle. The complex can be disaggregated using a variety of methods including, but not limited to, competitive, physical, chemical, enzymatic, or thermal dissociation.

The target cells bound to particles formed in step (b) above for either negative or positive selection can be separated from the non-magnetic non-target cells using a variety of techniques.

In the preferred embodiment, the particles are magnetic particles and the sample, containing the target cells labeled with magnetic particles, is placed into a magnetic field. The target cells labeled with magnetic particles migrate towards the magnetic field and are held in place allowing the non-magnetic non-target cells to be easily separated from the target cells labeled with magnetic particles.

The methods of the disclosure may be used in the processing of biological samples that contain erythrocytes including blood (in particular, cord blood and whole blood) bone marrow, fetal liver, buffy coat suspensions, leukapheresis samples, pleural and peritoneal effusions and suspensions of thymocytes and splenocytes. The method can be used to deplete erythrocytes from biological samples containing erythrocytes such as whole blood or whole bone marrow.

The method of the disclosure can be used to prepare enriched samples of any cell type including, but not limited to, T cells, B cells, NK cells, dendritic cells, monocytes, basophils, mast cells, progenitor cells, stem cells and tumor cells.

In one embodiment, the method of the disclosure may be used to prepare a cell preparation from samples such as blood and bone marrow, which is enriched in a selected differentiated cell type such as T cells, B cells, NK cells, monocytes, dendritic cells, basophils and plasma cells. This will enable studies of specific cell to cell interactions including growth factor production and responses to growth factors. It will also allow molecular and biochemical analysis of specific cells types. Cell preparations enriched in NK cells, dendritic cells and T cells may also be used in immune therapy against certain malignancies.

Antibody and Particle Compositions

The disclosure includes the antibody and particle compositions for use in the methods described herein.

The mono-specific TAC will contain (a) a first antibody that binds to an antigen on the target cell, linked indirectly, to (b) a second antibody that binds to the same target cell. The two antibodies can be identical or be different antibody clones of the same animal species that recognize a different epitope on the same antigen, or different antigens expressed on the same target cell.

In a preferred embodiment, at least one mono-specific TAC will be directly coupled to a particle using conventional techniques that are readily apparent to those skilled in the art such as physical adsorption or chemical conjugation.

The term "first antibody" and "second antibody" means that the antibody composition includes at least one type of antibody (as opposed to one antibody molecule). One type of antibody means an antibody that binds to a particular epitope on an antigen. For example, antibodies that bind to the antigen CD3 are considered one type of antibody.

In one aspect, the mono-specific TAC of the present disclosure comprises (a) one antibody specific for a target cell indirectly linked to (b) a second antibody specific for the same target cell. By "indirectly linked" it is meant that antibody (a) and antibody (b) are not directly covalently linked to each other but are attached through a linking moiety such as an immunological complex. In a preferred embodiment, the antibody composition contains at one antibody to the target cell (a) that is indirectly linked to a second antibody specific for the same target cell (b) by preparing a mono-specific tetrameric antibody complex. A mono-specific tetrameric antibody complex may be prepared by mixing the monoclonal antibody which is capable of binding to the target cells from a first animal species with an equimolar amount of monoclonal antibodies of a second animal species which are directed against the Fc-fragments of the antibodies of the first animal species. The antibodies from the first animal species may also be reacted with an about equimolar amount of the full length or F(ab')2 fragments of monoclonal antibodies of a second animal species which are directed against the Fc-fragments of the antibodies of the first animal species.

The term "at least one mono-specific TAG" means that at least one TAC is directly coupled to a single particle. In a preferred embodiment, a mono-specific TAC is specific for a single type of target entity such as a cell. In one embodiment, the mono-specific TAC contains two identical antibodies from a first animal species that recognize the same antigen epitope that are held in a tetrameric array by two antibodies from a second animal species that recognize the Fc-fragment of the first animal species. In another embodiment, the mono-specific TAC contains two different antibody clones from the first animal species that recognize different epitopes on the same target antigen that are held in a tetrameric array by two antibodies from a second animal species that recognize the Fc-fragment of the first animal species. In yet another embodiment, the mono-specific TAC contains two different antibody clones from the first animal species that recognize different antigens expressed on the same target cell, that are held in a tetrameric array by two antibodies from a second animal species that recognize the Fc-fragment of the first animal species.

The TAC coupled particles will be mixed with the sample under conditions to allow at least one TAC coupled particle to bind to one target cell.

In a preferred embodiment, mono-specific TAC specific for the target cells are directly coupled to the particle using conventional techniques that are readily apparent to those skilled in the art such as physical adsorption or chemical conjugation.

Within the context of the present disclosure, antibodies are understood to include monoclonal antibodies and polyclonal antibodies, antibody fragments (e.g., Fab, and F(ab') 2), chimeric antibodies, bifunctional or bispecific antibodies. Antibodies are understood to be reactive against a selected antigen on the surface of a target cell or erythrocyte if they bind with an appropriate affinity (association constant), e.g. greater than or equal to $10^7$ $M^{-1}$.

Monoclonal antibodies are preferably used in the antibody compositions of the disclosure. Monoclonal antibodies specific for selected antigens on the surface of nucleated cells may be readily obtained or generated using conventional techniques that are readily apparent to those of skill in the art.

The disclosure also contemplates aptamers or chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes selected antigens on the surface of differentiated cells or tumor cells. See for example, Kim and Hong [2].

The following non-limiting examples are illustrative of the present disclosure:

EXAMPLES

Example 1

Preparation of Tetrameric Antibody Complexes

In order to prepare a mono-specific tetrameric antibody complex for use in the method of the present disclosure, the following protocol may be used: (a) take 1 mg of antibody specific for an antigen on the target cells (e.g. anti-erythrocyte (glycophorin A), CD8, CD16, CD19, CD36, CD56, CD66b, etc.); (b) add 1 mg of P9 antibody or 0.68 mg of P9 F(ab')2 antibody fragment. Incubate overnight at 37° C. For more information on the preparation of tetramers see U.S. Pat. No. 4,868,109 to Lansdorp, which is incorporated herein by reference. Mono-specific tetrameric antibody complexes incorporating different antibodies to antigens expressed on different target cells are prepared separately.

Mono-specific TACs prepared with different antibodies are coupled separately to particles. A coupled particle cocktail is made by combining various coupled particles depending on which cells one wishes to deplete. The concentration of the various mono-specific TACs varies: typically antibodies to antigens expressed on nucleated cells are at 2.5-400 ug/mL in mono-specific TACs. The coupled particle composition is then diluted 1/20 into the cells so the final concentrations of each anti-cell antibody in the cell suspensions is between 0.125-20 ug/mL. The final concentration of each particle is between 0.05-5 mg/mL.

Example 2

Preparation of Mono-Specific TACs Coupled to Magnetic Particles

In order to prepare a particle with coupled monoclonal antibodies or mono-specific TACs for use in the method of the present disclosure, the following protocol may be used: (a) take 200 ug of anti-glycophorin A antibody alone, or 200 ug of anti-glycophorin A antibody bound in a tetrameric antibody complex with 200 ug of P9 antibody; (b) add 80 mg of carboxydextran magnetic particles; and (c) incubate overnight at 15-37° C. to facilitate passive adsorption of antibodies or mono-specific TACs onto the magnetic particle. The composition is then diluted 1/20 into the sample so the final concentration of anti-glycophorin A antibody is between 1-10 ug/mL. The final concentration of the magnetic particles is between 0.4-4 mg/mL.

In another embodiment, chemical crosslinking of antibodies or TACs to magnetic particles is performed using conventional techniques that are readily apparent to those of skill in the art. A non-limiting example illustrative of the present disclosure would be the EDC-NHS crosslinking of anti-glycophorin A mono-specific TAC to a carboxydextran magnetic particle. The anti-glycorphorin A mono-specific TAC coupled particle is then diluted 1/20 into the sample so the final concentration of anti-glycophorin A antibody in the mono-specific TAC is between 1-10 ug/mL.

Example 3

Method of Immunomagnetic Negative Cell Enrichment of Peripheral Blood Nucleated Cells from Human Peripheral Whole Blood Using Mono-Specific Tetrameric Antibody Complexes Specific for the Anti-Glycophorin A Directly Bound to Magnetic Particles A negative selection protocol for enriching peripheral blood nucleated cells from human peripheral whole blood using magnetic cell separation is set out below.
1. Add 50 uL of mono-specific glycophorin A TACs coupled to magnetic particles per mL of human peripheral whole blood.
2. Incubate 5 minutes at room temperature.
3. Dilute sample with a volume of phosphate buffered saline (PBS) equivalent to the starting whole blood sample and mix gently.
4. Place the tube containing the sample into a magnet.
5. Incubate 5 minutes at room temperature.
6. Remove the enriched cells from the sample while the sample tube is retained within the magnet.
7. Add an equivalent volume of coupled particles as in step 1 to the diluted enriched sample
8. Incubate 5 minutes at room temperature.
9. Place the tube containing the sample into a magnet.
10. Incubate 5 minutes at room temperature.
11. Remove the enriched cells from the sample while the sample tube is retained within the magnet.
12. The desired cells are now in a new tube and ready for use.

This example demonstrates that erythrocytes that are the major component of human whole blood can be depleted using the aforementioned method using anti-glycophorin A monospecific TACs coupled to magnetic particles. As shown in FIG. 1B), following erythrocyte depletion using glycophori-A monospecific TACs coupled to magnetic particles using the method described above, 99.05% of enriched cells are CD45+GlyA− compared to 99.95% CD45-GlyA+ when magnetic particles alone are added to human whole blood.

Example 4

Method of Immunomagnetic Positive Selection of Granulocytes from Human Peripheral Whole Blood Using Mono-Specific Tetrameric Antibody Complexes Specific for the Anti-CD66b Directly Bound to Magnetic Particles A positive selection protocol for isolating granulocytes from human peripheral whole blood using magnetic cell separation is set out below.
1. Add 5 uL of mono-specific anti-CD66b TACs coupled to magnetic particles per mL of human peripheral whole blood.
2. Incubate 5 minutes at room temperature.
3. Dilute the sample with a volume of PBS equivalent to the starting whole blood sample and mix gently.
4. Place the tube containing the sample into a magnet.
5. Incubate 5 minutes at room temperature.
6. Remove the supernatant containing the undesired cells from the sample while the sample tube containing the desired cells is retained within the magnet.
7. Remove the tube containing the desired cells from the magnet and resuspend the sample tube containing the desired cells with PBS.
8. Repeat steps 4-7 twice more for a total of three 5 minute magnetic separations.
9. The desired cells labelled with the coupled particles are now ready for use.

Figure 3:
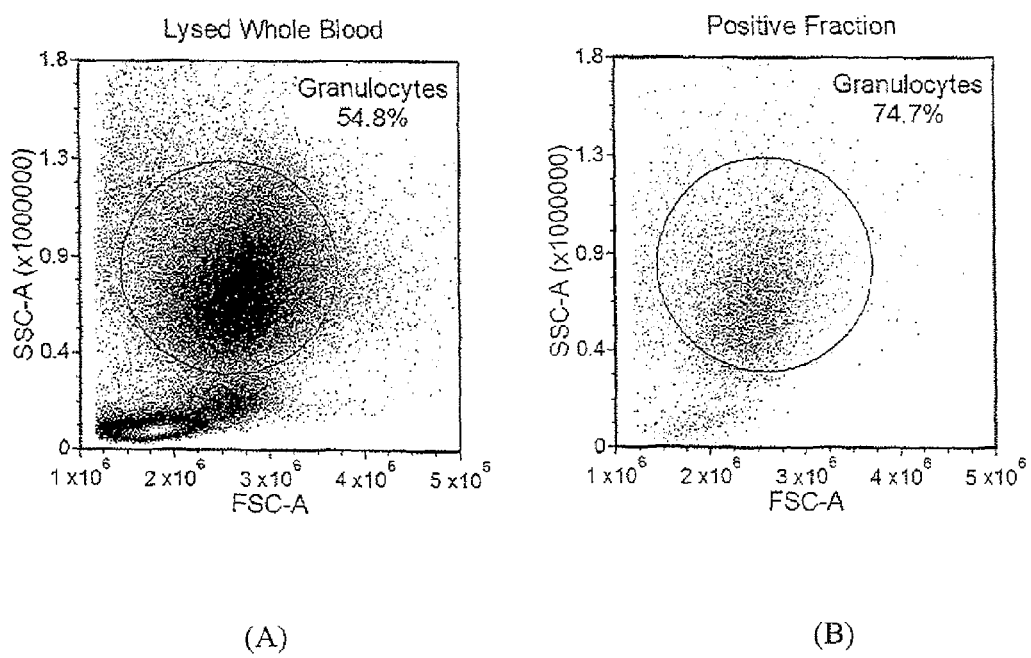
FIG. 3 shows the positive selection of CD66b+ granulocytes from human peripheral whole blood using mono-specific anti-CD66b TACs coupled to magnetic particles. (A) shows that granulocytes can be positively selected and enriched to 54.8% and (B) shows that granulocytes can be positively selected and enriched to 74.7%.

This example demonstrates that granulocytes can be positively selected from human whole blood using anti-CD66b monospecific TACs coupled to magnetic particles. As shown in FIG. 3, granulocytes can be positively selected and enriched to 74.7% using the method described above.

Example 5

Comparison of Human Erythrocyte Depletion with Anti-Glycophorin A Antibodies Coupled to Magnetic Particles Versus Anti-Glycophorin A Mono-Specific TACs Coupled to Magnetic Particles This example demonstrates the immunomagnetic depletion of erythrocytes from human whole blood using magnetic particles coupled to either anti-glycophorin A antibodies or anti-glycophorin A mono-specific TACs (FIG. 1). Erythrocytes in human whole blood were depleted using the method described in example 3 using either monoclonal antibody or mono-specific TAC coupled magnetic particles specific for glycophorin A. Anti-glycophorin A mono-specific TACs were prepared as described in example 1. Coupled magnetic particles with either anti-glycophorin A monoclonal antibodies or mono-specific TACs were prepared as described in example 2. A) Images of the final sample comparing (from left to right) magnetic particles alone without any antibodies, mono-specific anti-glycophorin A TAC coupled to magnetic particles, equivalent concentration of anti-glycophorin A monoclonal antibodies coupled to the equivalent amount of magnetic particles, and double the concentration of anti-glycophorin A monoclonal antibodies coupled to the equivalent amount of magnetic particles. Doubling the concentration of anti-glycophrin A results in the equivalent total antibody concentration if the crosslinking anti-mouse IgG1 antibody is taken into consideration for the mono-specific TAC. The only sample that efficiently depleted erythrocytes, was the sample separated with the mono-specific anti-glycophorin A TACs coupled to the magnetic particles. B) The enriched samples were stained with anti-glycophorin A (GlyA) FITC and anti-CD45 APC and analyzed by flow cytometry to determine the degree of erythrocyte depletion by assessing the percentage of CD45+/GlyA− cells in the enriched sample. Magnetic particles alone resulted in 0.03% of CD45+/GlyA− cells. Mono-specific anti-glycophorin A TAC coupled magnetic particles resulted in 99.05% CD45+/GlyA− cells. In comparison, the equivalent concentration of monoclonal anti-glycophorin A antibody coupled to the magnetic particles resulted in only 0.35% CD45+/GlyA−. Doubling the concentration of glycophorin A monoclonal antibodies resulted in a minor increased of CD45+/GlyA− cells to 3.51%.

Example 6

Figure 2:
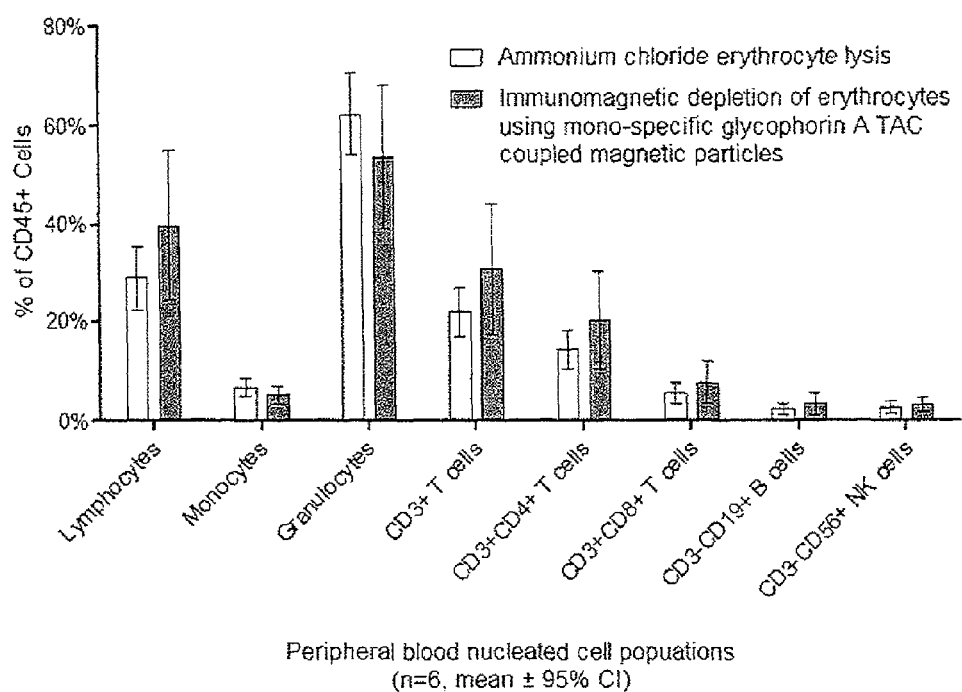
FIG. 2 compares the enrichment of human peripheral blood nucleated cells using either immunomagnetic erythrocyte depletion using mono-specific TAC coupled magnetic particles or ammonium chloride lysis of erythrocytes.

Comparison of the Enriched Peripheral Blood Nucleated Cells Following Either Immunomagnetic Depletion of Erythrocytes Using Mono-Specific Glycophorin A TACs Compared to Ammonium Chloride Hypotonic Lysis of Erythrocytes in Human Whole Peripheral Blood The example demonstrates that the immunomagnetic enrichment of human peripheral blood nucleated cells using mono-specific glycophorin A TAC coupled to magnetic particles results in similar frequencies of cell populations as compared to a standard ammonium chloride lysis procedure (FIG. 2). Erythrocytes were depleted using either the method according to example 3 or standard ammonium chloride hypotonic lysis and washing. Enriched samples were stained with anti-CD4 or CD19 FITC, anti-CD8 or CD56 PE, anti-CD3 PerCP-Cy5.5 and anti-CD45 APC and analyzed by flow cytometry. Samples were gated on CD45+ cells and populations were identified either by FSC/SSC gating or by expression of cell surface markers (n=6).

Example 7

Immunomagnetic Positive Selection of Granulocytes from Human Peripheral Whole Blood Using Anti-CD66b Mono-Specific TACs Coupled to Magnetic Particles The example demonstrates the immunomagnetic positive selection of granulocytes from human whole blood using mono-specific anti-CD66b TACs coupled to magnetic particles according to the method described in example 4 (FIG. 3). Ammonium chloride lysed whole blood and positively selected samples were stained with anti-CD45 and analyzed by flow cytometry. Samples were gated on CD45+ cells and granulocytes were identified based on high FSC and SSC gating. In the start whole blood sample, 54.8% of the CD45+ cells were granulocytes. Following immunomagnetic positive selection, 74.7% of the CD45+ cells were granulocytes.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

1. Rabe, M., Verdes, D., and Seeger, S. (2011). Understanding protein adsorption phenomena at solid surfaces. Advances in Colloid and Interface Science. 162. 87-106.
2. Kim, J. H., and Hong, H. J. (2012). Humanization by CDR Grafting and Specificity-Determining Residue Grafting. In P. Chames (Ed.), *Antibody Engineering: Methods and Protocols* ($2^{nd}$ Edition. pp. 237-245). New York: Humana Press

What is claimed is:

1. A method of separating target entities from a sample comprising target entities and non-target entities, said method comprising:
    (a) providing at least one mono-specific tetrameric antibody complex (TAC) coupled to a surface, wherein the TAC comprises two antibodies, each antibody specifically binding to the same target entities and wherein the TAC does not comprise bi-specific TACs;
    (b) contacting the sample with the TAC coupled surface under conditions to allow the antibodies of the TAC coupled surface to specifically bind to the target entities to form a target entities-TAC coupled surface complex; and
    (c) separating the target entities-TAC coupled surface complex from the sample to separate the target entities from the non-target entities.

2. The method according to claim 1, wherein the surface is a flask, column of beads; or particles.

3. The method according to claim 2, wherein the surface is a particle.

4. The method according to claim 3, wherein the particle is non-magnetic.

5. The method according to claim 3, wherein the particle is magnetic.

6. The method according to claim 5, wherein the target entities bound to the TAC of the TAC coupled magnetic particles are separated by placing said sample into a magnetic field to separate the target entities from the non-target entities.

7. The method according to claim 1, wherein the target entities are selected from the group consisting of cells, bacteria, viruses, cell organelles, proteins and nucleic acids.

8. The method according to claim 7 wherein the target entities are cells.

9. The method according to claim 8, wherein the cells are selected from the group consisting of erythrocytes, lymphocytes, monocytes, granulocytes, tumor cells, stem cells, hematopoietic progenitor cells, mesenchymal cells, mammary epithelial cells, neural cells, and endothelial progenitor cells.

10. The method according to claim 9 wherein the cells are granulocytes.

11. The method according to claim 10 wherein the monospecific TAC comprises anti-CD66 antibodies.

12. The method according to claim 9 wherein the stem cells are endothelial stem cells or embryonic stem cells.

13. The method according to claim 9 wherein the cells are erythrocytes.

14. The method according to claim 13 wherein the monospecific TAC comprises anti-glycophorin A antibodies.

* * * * *